(12) United States Patent
Butterfield

(10) Patent No.: US 8,323,007 B2
(45) Date of Patent: Dec. 4, 2012

(54) FLUID PUMP WITH DISPOSABLE COMPONENT

(75) Inventor: Robert D. Butterfield, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 13/306,671

(22) Filed: Nov. 29, 2011

(65) Prior Publication Data

US 2012/0141306 A1    Jun. 7, 2012

Related U.S. Application Data

(63) Continuation of application No. 11/832,612, filed on Aug. 1, 2007, now Pat. No. 8,087,906.

(51) Int. Cl.
*F04B 17/00* (2006.01)
(52) U.S. Cl. .................................................. 417/413.1
(58) Field of Classification Search .................. 417/395, 417/412, 413.1, 413.2
See application file for complete search history.

(56) References Cited

U.S. PATENT DOCUMENTS

| | | | | |
|---|---|---|---|---|
| 5,554,013 A | * | 9/1996 | Owens et al. | 417/413.1 |
| 6,685,444 B2 | * | 2/2004 | Ogawa | 417/413.1 |
| 7,713,034 B2 | * | 5/2010 | Ogawa | 417/413.1 |

FOREIGN PATENT DOCUMENTS

| | | | |
|---|---|---|---|
| DE | 3813374 | * | 11/1989 |
| JP | 02-223686 | | 9/1990 |
| JP | 2004-353493 | | 12/2004 |
| JP | 2006-161648 | | 6/2006 |
| WO | WO2005111423 | * | 5/2005 |

OTHER PUBLICATIONS

Office Action for Japanese Patent Application No. 2010-519179 mailed Jul. 13, 2012.

* cited by examiner

*Primary Examiner* — Devon Kramer
*Assistant Examiner* — Bryan Lettman
(74) *Attorney, Agent, or Firm* — McDermott Will & Emery LLP

(57) ABSTRACT

A pump having a disposable fluid contacting portion which defines a fluid inlet and outlet and a fluid path there between is presented. The pump includes a drive portion configured to engage the disposable portion to cause fluid to be moved from the fluid inlet to the fluid outlet. The disposable portion is configured to be selectively coupled to the drive portion. The disposable portion includes a driven membrane which forms a portion of the fluid path, and the drive portion includes a drive membrane. The two membranes are vacuum coupled to each other, whereby movement of the drive membrane causes the driven membrane to move, causing fluid to be pumped through the disposable portion. The pump has particular utility in the medical field for moving fluid from a source to a patient. The pump may include features such as an air-trap, bubble detection, fluid flow controls, and pressure detection.

14 Claims, 8 Drawing Sheets

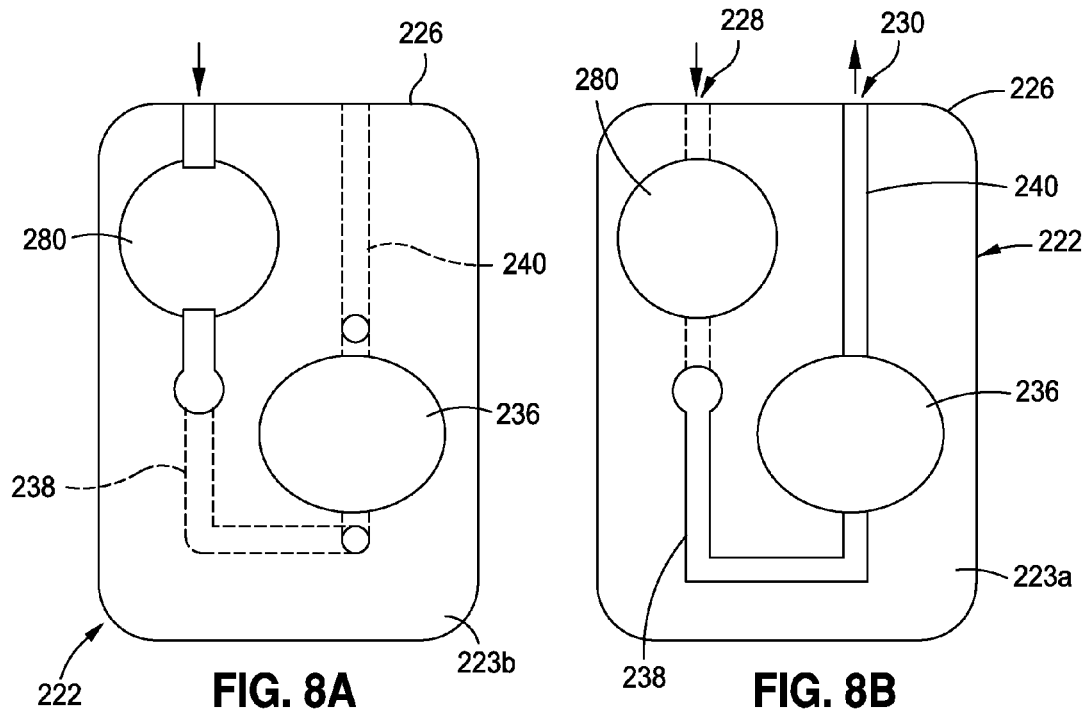
FIG. 8A
FIG. 8B
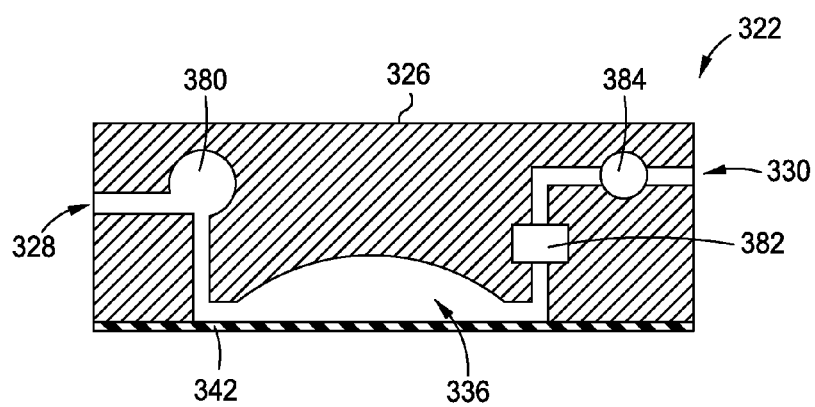
FIG. 8C

FLUID PUMP WITH DISPOSABLE COMPONENT

This application is a continuation of U.S. application Ser. No. 11/832,612, filed Aug. 1, 2007 and now issued as U.S. Pat. No. 8,087,906, which is hereby incorporated by reference in its entirety.

FIELD OF THE INVENTION

The present invention relates to fluid pumps, especially to medication delivery pumps.

BACKGROUND OF THE INVENTION

A wide variety of medication delivery pumps are known. In general, these pumps are configured to deliver a fluid from a source to a patient under pressure.

In order for the pump to be re-usable, at least the portion of the pump which contacts the fluid must be sterilizable. This is difficult for integral pumps where the pumping mechanism and fluid path are part of a single unit. For this reason, pumps have been developed with have a re-usable pumping unit which cooperates with a fluid path element. In this manner, the fluid path element can be separated from the pumping unit for sterilization and reuse.

These reusable pumps, however, suffer from a number of drawbacks. First, many designs are highly complex, resulting in high costs of manufacture and maintenance costs, and low reliability. In addition, the pumps generally suffer from one or more design issues which result in less than optimum performance. For example, it is desirable for the pump to include a flow sensor, and yet such a feature is often inconsistent with the design of the re-usable pump. Also, these pumps generally have undesirable compliance. "Compliance" is a measure of the volume per unit pressure change in region between intake and outlet of the pump. Many commercial pumps suffer significantly due to undesirable compliance resulting in either significant change to average and instantaneous flow when varying intake and output pressures are experienced.

For example, one re-usable pump design is represented by the IVAC 500 series (550, 570, 580, etc.) linear peristaltic pumps. These pumps use sequentially occluding fingers to peristaltically advance fluid by advancing an occlusion point from the intake end to the outlet end of a second of tubing. Compliance of the tubing governs the sensitivity of average flow to intake pressure. The average flow of these pumps is quite insensitive to output pressure. However, flow uniformity is degraded with increasing output pressure and pump segment compliance.

Other examples of re-usable pumps are the Alaris LVP Module and Asena GP pumps. These are dual chamber pumps using conventional cylindrical tubing together with two active pumping regions and two valves, one above the upper region and the second between the upper and lower pumping region. The net filling volume of the upper pump region defines the cyclic volume pumped and due to the elasticity of this region, variation of intake pressure affects the actual volume delivery. The lower pump region delivers fluid while the upper chamber is filling, resulting in smoothing of flow output. If elevated output pressure exists, when the lower occlude opens, fluid moves retrograde into the upper pump region. When the upper occluder opens, this excess volume moves back into the drip chamber, thus reducing net volume pumped and disturbing uniformity of flow. A second drawback of dual chamber pumps is the likelihood of air being entrained within the pumping chambers. When this occurs, not only is the compliance increased, but the net pumping volume is directly diminished.

SUMMARY OF THE INVENTION

One aspect of the invention is a fluid pump and a method of pumping or moving fluid.

One embodiment of a fluid pump comprises a drive unit and a driven unit. The drive unit comprises a housing, a drive or driving membrane and at least one drive device configured to move the driving membrane between at least a first and a second position. The driven unit is preferably configured as the fluid contacting portion of the pump, and thus comprises a disposable portion of the pump. The driven unit comprises a housing, a fluid path leading from a fluid inlet to a fluid outlet, and at least one driven membrane defining at least a portion of the fluid path.

The driven unit is configured to be selectively coupled to the drive unit so that the driven membrane is coupled to the driving membrane, whereby movement of the driving membrane effectuates movement of the driven membrane, causing fluid to be pumped through the driven unit from the fluid inlet to the fluid outlet. Preferably, the driving and driven membranes are vacuum coupled, such as by applying a vacuum source to a vacuum path or line extending to the interface of the membranes.

The drive unit includes a drive device configured to move the driving membrane. In one embodiment, the driving membrane forms a portion of a boundary of a variable volume fluid chamber. The drive device includes a piston or other member for changing the volume of the chamber. In another embodiment, the driving membrane is moved directly, such as a by one or more actuators.

The pump may include fluid flow controls, such as a fluid inlet and fluid outlet valve or control. The pump may also include such features as an air trap, bubble detector, pressure sensor(s), and fluid line connectors.

One embodiment of a method comprises providing a drive unit and disposable or driven unit and connecting the driven unit with the drive unit so that a driven membrane of the disposable unit is positioned adjacent a driving membrane of the drive unit. The method further comprises vacuum coupling the driven membrane to the driving membrane and moving the driving membrane, whereby the driven membrane is moved therewith, causing fluid to be pumped through the driven unit from a fluid inlet to a fluid outlet.

Further objects, features, and advantages of the present invention over the prior art will become apparent from the detailed description of the drawings which follows, when considered with the attached figures.

BRIEF DESCRIPTION OF THE DRAWINGS

FIG. 8A is a bottom view of a disposable portion of a fluid pump in accordance with another embodiment of the invention;

FIG. 8B is a top view of the disposable portion illustrated in FIG. 8A;

FIG. 8C is a cross-section of another embodiment of a disposable portion of a fluid pump in accordance with the present invention.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In general, the invention comprises a fluid pump. The pump has particular utility to the medical field, such as for use in pumping medication from a source to a patient. In general, the pump has a first, disposable portion, and a second, drive portion. The disposable portion is preferably configured as the fluid contacting portion and defines a fluid inlet and outlet and a fluid path therebetween. The drive portion is configured to engage the disposable portion to cause fluid to be moved from the fluid inlet to the fluid outlet. The disposable portion is configured to be selectively coupled to the drive portion. In one embodiment, the disposable portion and the drive portion are vacuum coupled.

Figure 1:
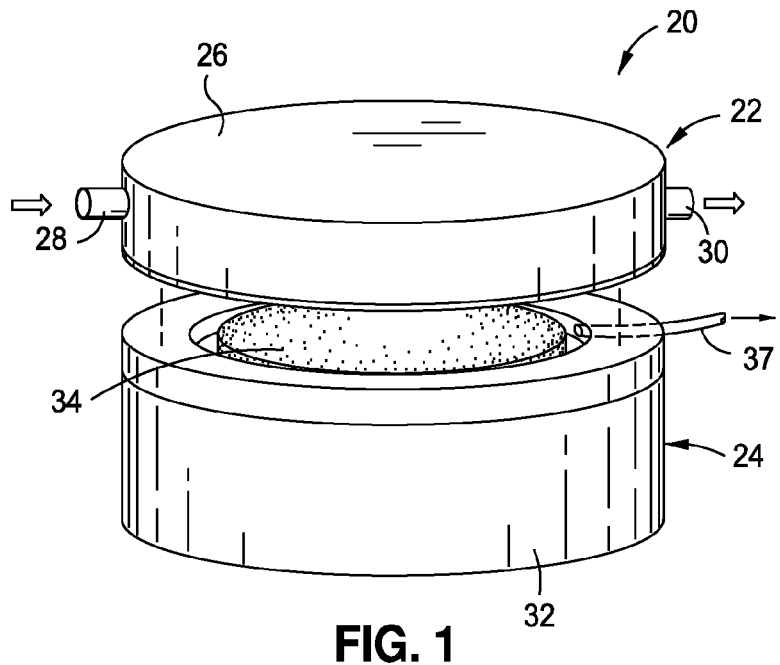
FIG. 1 is a perspective view of a fluid pump in accordance with an embodiment of the invention.

The invention will first be described with reference to FIGS. 1-3, which illustrate one embodiment of the invention in a conceptual or basic configuration. As illustrated in FIG. 1, a fluid pump 20 preferably comprises a driven unit or portion 22 and a drive unit or portion 24. In a preferred embodiment, the driven portion 22 is configured to be disposable (i.e. used a limited number of times, such as once, in conjunction with the drive portion, and then discarded), and as such is referred to herein as a disposable unit or portion.

In one embodiment, the disposable portion 22 comprises a housing 26 which defines a fluid inlet 28 and a fluid outlet 30. The drive portion 24 similarly comprises a housing 32 and at least one drive element 34. In a preferred embodiment, the disposable portion 22 and drive portion 24 are configured to be vacuum coupled. As such, the drive portion 24 may include a vacuum path 37.

Figure 2:
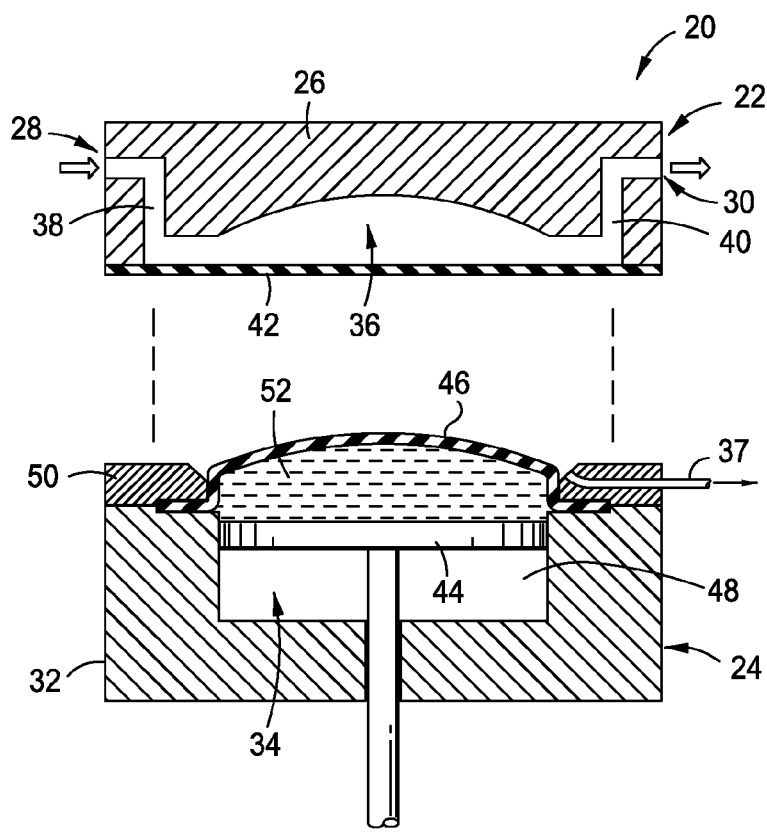
FIG. 2 is a cross-sectional side view of the pump illustrated in FIG. 1, with a disposable portion of the pump separated from a drive portion thereof.
Figure 3:
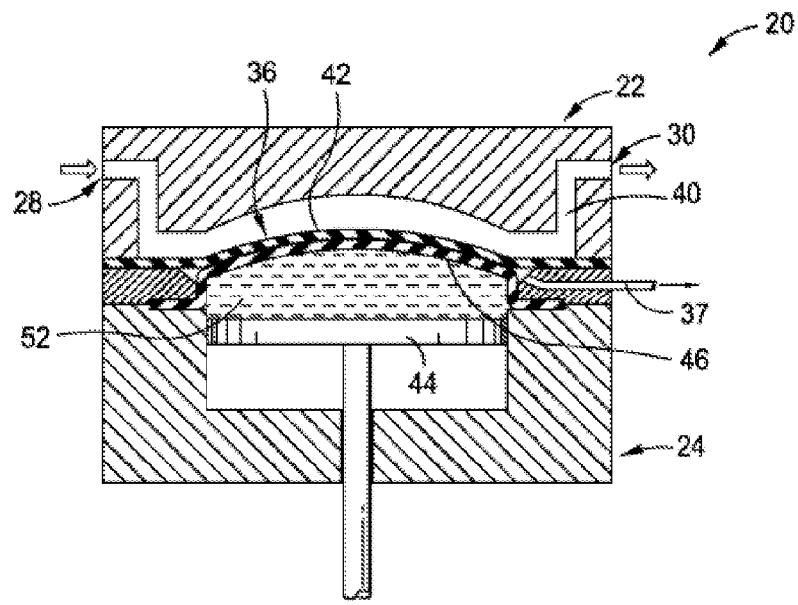
FIG. 3 illustrates the pump of FIG. 2 with the disposable portion of the pump mounted to the drive portion, and the pump in first pumping condition.

In FIGS. 1-3, the housings 26,32 of the disposable portion 22 and drive portion 24 of the pump 20 are illustrated as being generally cylindrical in shape. As detailed herein, the disposable portion 22 and drive portion 24 may have a variety of configurations.

Referring to FIG. 2, in one embodiment, the disposable portion 22 has a top and a bottom. The bottom is configured to mate with a top of the drive portion 24 of the pump 20. The disposable portion 22 and drive portion 24 could be configured to mate or connect in other manners or positions, such as in a side-by-side configuration or where the drive portion 24 is mounted on the disposable portion 22.

A fluid pathway is defined from the fluid inlet 28 to the fluid outlet 30 of the disposable portion 22. Preferably, this fluid pathway is defined by the housing 26. In one embodiment, this fluid pathway comprises a pump chamber 36, a fluid inlet pathway 38 leading from the fluid inlet 28 to the pump chamber 36, and a fluid outlet pathway 40 leading from the pump chamber 36 to the fluid outlet 30. In one embodiment, the fluid inlet and outlet pathways 38,40 are passages through the housing 26.

As illustrated, the pump chamber 36 comprises a recessed area of the bottom of the housing 26 of the disposable portion 26. In one embodiment, the recessed area is generally dome or hemi-spherical in shape (i.e. having a perimeter which is circular in shape, but varying in diameter along its depth). In addition, the pump 20 comprises a first or driven membrane 42. In one embodiment, the driven membrane 42 spans or covers the recessed area of the disposable portion 22, thus enclosing that portion to form the pump chamber 36 or otherwise forming at least a portion of the boundary of the pump chamber 36. As detailed below, the driven membrane 42 preferably comprises a flexible and resilient member which is configured to move relative to the housing 26 of the disposable member 22.

The drive element 34 of the drive portion 24 is preferably configured to selective move the driven membrane 42 relative to the housing 26 of the disposable portion 22, thereby changing the volume of the pump chamber 36. In this manner, as detailed below, fluid is pumped from the inlet 28 to the outlet 30 of the disposable portion 22.

As detailed herein, the drive element 34 may comprise a wide variety of elements or mechanisms. As illustrated in FIG. 2, the drive element 34 comprises a drive or driving membrane 46 movable in response to movement of a piston 44 which is movably located in a portion of the housing 32 of the drive portion 24 of the pump 20. In this configuration, the driving membrane 46 is fluid driven. In particular, the driving membrane 46 is associated with a variable volume fluid chamber 48, and preferably comprises a boundary portion thereof. The piston 44 also defines at least a portion of the chamber 48, and in that the piston 44 is moveable (such as between extended and retracted positions), the volume of the chamber 48 may be varied. Preferably, the driving membrane 46 is connected to the housing 32 of the drive portion 24, such as by positioning a periphery of the driving membrane 46 between a top portion of the housing 32 and a retainer 50 selectively coupled to the housing 32.

Fluid 52 is located between a top of the piston 44 and the driving membrane 46. As detailed below, movement of the piston 44 causes the driving membrane 46 to move in and out (the range of movement may vary, such as depending upon desired flow rate, wherein the movement may be between convex, concave and/or neutral or flat positions relative to the housing), thus moving the driven membrane 42 of the disposable portion 22 of the pump 20. As detailed below, one or more mechanisms may be provided for moving the piston 44.

The driven membrane 42 and driving membrane 46 are configured to move with one another. In a preferred embodiment, the drive membrane 46 and driven membrane 46 are coupled to one another. Various means may be utilized for this purpose. Preferably, the means allows the disposable portion 22 of the pump 20 to be selectively connected to, and disconnected from (such as for connection of another disposable portion) the drive portion 24 of the pump.

In one embodiment, the driven membrane 42 and driving membrane 46 are vacuum coupled. As indicated, a vacuum pathway 37 is provided for this purpose. The vacuum pathway 37 preferably leads from a vacuum source to a region adjacent the drive membrane 46 (and the driven membrane 42 or the interface of the driven membrane 42 and driving membrane 46 when the disposable portion 22 is connected to the drive portion 24 of the pump 20). As detailed below, a vacuum applied through the pathway 37 preferably vacuum couples the driven membrane 42 and driving membrane 46.

A method of pumping in accordance with the invention will now be described with reference to FIGS. 3 and 4. In general, activation of the drive element 34 causes the volume of the pump chamber 36 to vary, thus causing fluid to be drawn into the fluid inlet 28 and expelled out the fluid outlet 30. In use, a disposable portion 22 is mounted or connected to a drive portion 24. A vacuum is then applied to vacuum couple the driven membrane 42 to the driving membrane 46, such as by connecting the vacuum line 37 to a vacuum source.

Figure 4:
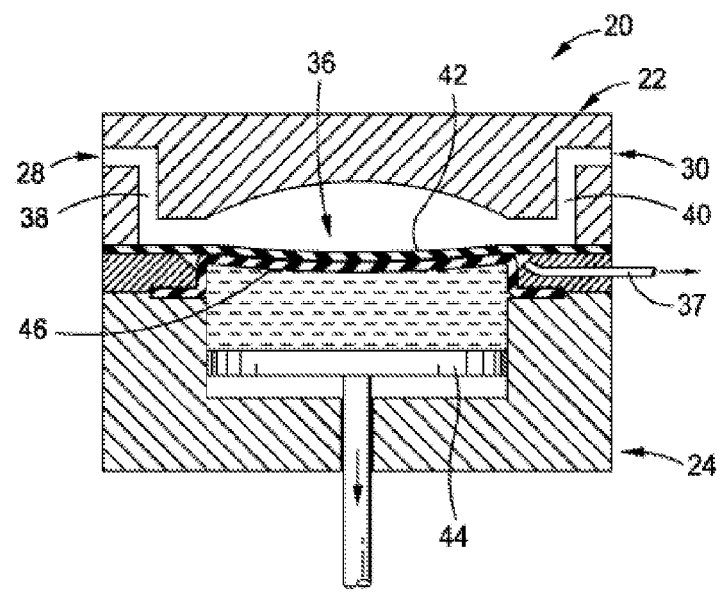
FIG. 4 illustrates the pump of FIG. 2 in a second pumping condition.

Referring to FIG. 4, when the piston 44 is moved downwardly, the volume of the fluid chamber increases. This draws the driving membrane 46, and thus the driven membrane 42 coupled thereto, downwardly. This increases the volume of the pump chamber 36, causing fluid to be drawn through the fluid inlet 28 and along the fluid inlet pathway 38 to the pump chamber 36.

As illustrated in FIG. 3, when the piston 44 is moved upwardly, the volume of the fluid chamber 48 decreases, causing the fluid pressure to increase, forcing the driving membrane 46 upwardly or outwardly. This causes the driven membrane 42 to move inwardly, thus reducing the volume of the pump chamber 36. This causes fluid to be displaced from the pump chamber 36 through the fluid outlet pathway 40 to the fluid outlet 30. In this regard, it is noted that while the pressure of the fluid in the pumping chamber 48 of the drive portion 24 of the pump increases (as a result of movement of the piston 44 reducing the volume of that chamber while the volume of fluid therein remains static), the fluid pressure in the actual fluid pump chamber 36 may or may not increase, although the volume of that chamber decreases thus causing fluid to be pumped through the pump (for example, the change in fluid pressure in the actual fluid pump chamber may be negligible or low when the fluid outflow resistance is relatively low and the overall fluid flow rate through the pump is relatively high).

As detailed below, in one embodiment, means may be provided for selectively controlling the flow of fluid through the driven portion 22 of the pump. Preferably, this means is configured to prevent the back-flow of fluid from the pump chamber 36 to the fluid inlet 28.

In operation, repeated cycling of the piston 44 effects pumping which causes a stream or flow of fluid through the pump 20.

Figure 5:
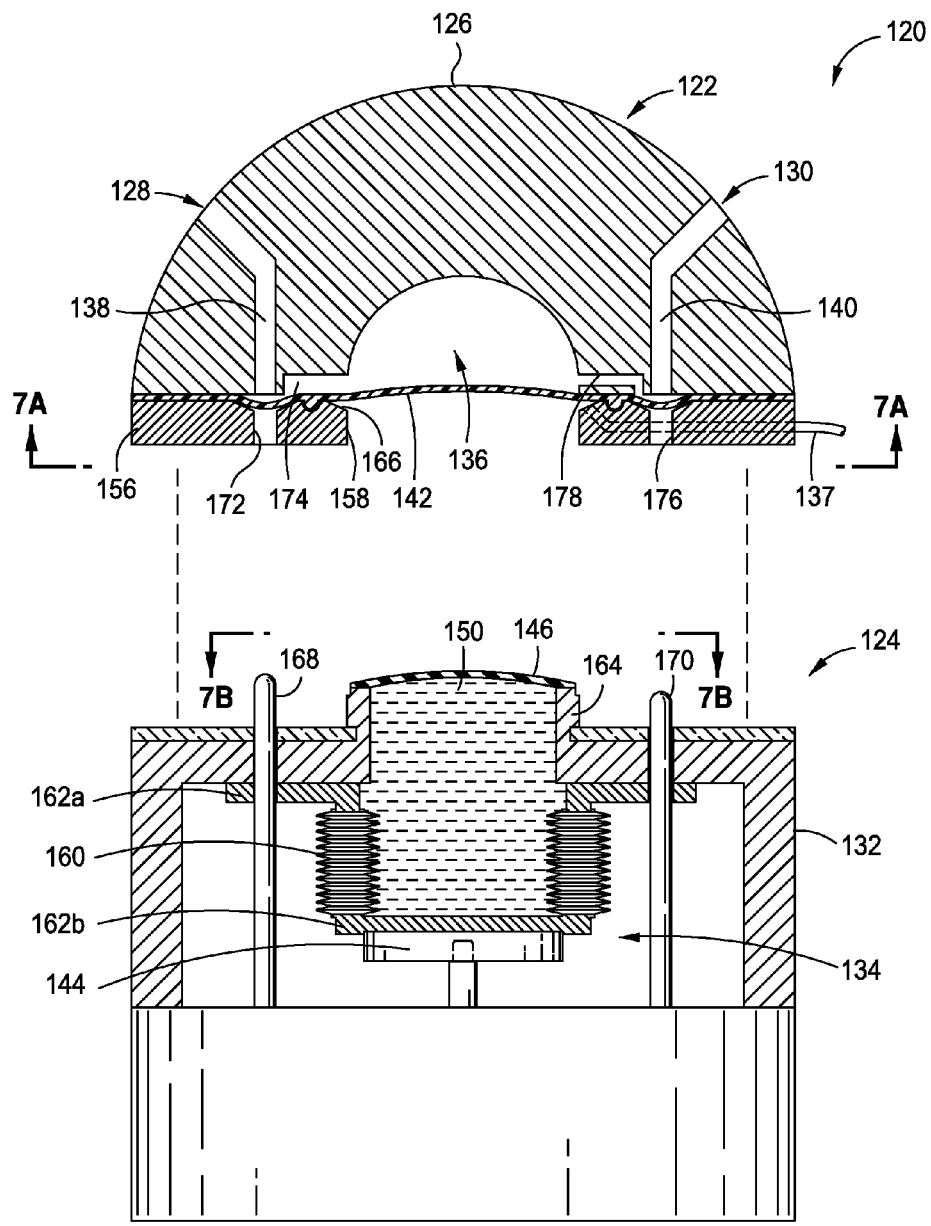
FIG. 5 is a cross-sectional side view of a vacuum coupled fluid pump in accordance with another embodiment of the invention, showing a disposable portion of the pump separated from a drive portion thereof.
Figure 6:
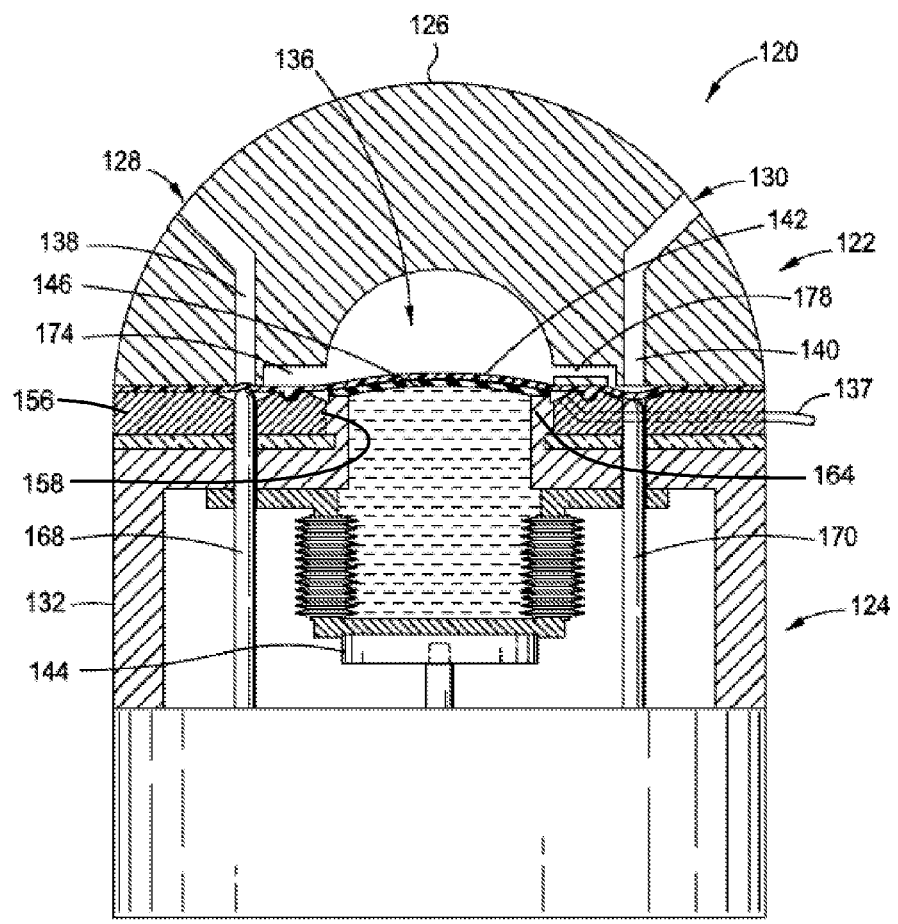
FIG. 6 illustrates the pump of FIG. 5 with the disposable portion of the pump mounted to the drive portion.

Another embodiment of the invention is illustrated in FIGS. 5 and 6. This embodiment pump 120 similarly comprises a first or disposable unit or portion 122 and a second or drive unit or portion 124. As illustrated, in this embodiment, a housing 126 of the disposable portion 122 is generally hemispherical in shape, having a domed top surface and (except as detailed below) a generally flat bottom surface. A fluid inlet pathway 138 leads from a fluid inlet 128 in the top of the housing 126 to the bottom of the housing 126. Likewise, a fluid outlet pathway 140 leads from the bottom of the housing 126 to a fluid outlet 130 at the top of the housing. In one embodiment, the fluid inlet 128 and fluid outlet 130 are located in the same plane, at opposing sides of the housing 126.

Once again, a pump chamber 136 is defined at the bottom of the disposable portion 122 of the pump 120. The pump chamber 136 is, as illustrated, a somewhat hemi-spherical chamber extending into the bottom of the housing 126. A driven membrane 142 extends over the bottom of the housing 126, thus cooperating with the housing 126 to generally enclose the pump chamber 136.

The driven membrane 142 preferably comprises a flexible and yet resilient member. In one embodiment, as illustrated, the driven membrane 142 is approximately the same size as the bottom of the housing 126 of the disposable portion 122 of the pump 120. The driven membrane 142 may thus be generally circular in shape. The membrane 142 may be secured to the housing 126 by a lock ring 156. Preferably, the lock ring 156 is generally ring-shaped, having a central opening 158 corresponding to the fluid chamber 136. The lock ring 156 preferably engages the housing 126 such that at least a portion of the periphery of the driven membrane 142 is positioned there between.

The drive portion 124 of the pump 120 again comprises a housing 132 and a drive element 134. In one embodiment, the housing 132 is generally cylindrical in shape, having a cylindrical outer wall with a top and a bottom. The drive element 134 comprises a drive or driving membrane 146. Means are provided for moving the driving membrane 146. In one embodiment, this comprises a piston 144 and fluid 150. In the embodiment illustrated, a piston 144 is configured to move up and down relative to the housing 132 of the drive portion 124, such as within a chamber defined in an interior area thereof. A variable volume fluid chamber is defined by the housing 132, the drive membrane 146, and a bellows 160 and associated mount.

As illustrated, the bellows 160 is located between a top mount 162a and a bottom mount 162b, the bottom mount 162b being connected to or otherwise configured to move with the piston 144. In one embodiment, the bottom mount 162b might simply comprise the head of the piston 144 and the top mount 162a might comprise a portion of the housing 132. The bellows 160 comprises an accordion-like expandable and contractable member, whereby expansion and contraction of the bellows 160 via movement of the piston 144 causes the volume of the fluid chamber to change (thus changing the pressure of the fluid therein and the location of the driving membrane 146).

The pump 120 is configured so that the driving membrane 146 engages the driven membrane 142. In the embodiment illustrated, where the driven membrane 142 is inset from the bottom of the lock ring 156, the driving membrane 146 may be located outwardly of the top of the housing 132 of the drive portion 124. As illustrated, the housing 132 includes a flange or mount 164 which extends upwardly from the remainder of the top portion of the housing 132. The driving membrane 146 extends across this mount 164. Preferably, the mount 164 is sized to fit within the opening 158 of the lock ring 156 so that: (1) a seal is defined between the mount 164 and lock ring 156; and (2) the driving membrane 146 and driven membrane 142 engage one another.

As indicated above, means are preferably provided for selectively coupling the driving and driven membranes so that they move with one another, and yet which allows the disposable portion 122 of the pump 120 to be removed from the drive portion 124 in a manner allowing the drive portion 124 to be re-used with another disposable portion 122. In one embodiment, this means comprises a vacuum seal created by a vacuum device or source (not shown) via a vacuum line 137. The vacuum line 137 leads from the vacuum device or source to an interface between the driven membrane 142 and the driving membrane 146. As illustrated, the vacuum line 137 extends through the lock ring 156 (such as comprising a passage formed therein), and leading to the opening 158 therein. The vacuum line 137 may terminate at a sloping or recessed portion of the lock ring 158 at a point below the driven membrane 142. As detailed below, this permits air to be drawn from the space between the driving membrane 146 and driven membrane 142, thus vacuum coupling the two membranes to one another.

Preferably, the pump 120 is configured to control the flow of fluid between the fluid inlet pathway 138 and the fluid chamber 136, and the fluid chamber 136 and the fluid outlet pathway 140. In particular, it is desired that the pump 120 be configured so that when fluid is drawn into the fluid chamber 136, it is drawn through the fluid inlet pathway 138, and not backwardly through the fluid outlet pathway 140. Likewise, when fluid is pumped out of the fluid chamber 136, it is preferably delivered through the fluid outlet pathway 140, and not back to the fluid inlet through the fluid inlet pathway 138.

In one embodiment, one or more valves or other fluid flow controls are provided for this purpose. As illustrated in FIG. 5, the pump 120 includes a fluid inlet valve or control and a fluid outlet valve or control. In a preferred embodiment, the inlet and outlet valves take advantage of the driven membrane 142, and in particular, cause utilize the membrane 142 to selectively open and close fluid paths leading to and from the fluid chamber 136. In the embodiment illustrated, a portion of the driven membrane 142 can selectively be moved so as to open or close the end of the fluid intake pathway 138 at the bottom of the housing 126 of the disposable portion 122. Likewise, a portion of the driven membrane 142 can be moved so as to open or close the end of the fluid outlet pathway 140 at the bottom of the housing 126.

In the embodiment illustrated, a mechanism is provided for selectively moving the portions of the driven membrane 142 between the fluid pathway opening and closing positions. In a preferred embodiment, this mechanism comprises one or more actuators.

As illustrated, an inlet actuator 168 is configured to move between extended and retracted positions (or up and down as illustrated in the figures), thereby moving the driven membrane 142 up and down in the region of the fluid inlet pathway 138. As illustrated, the inlet actuator 168 is push-rod type element having a nose or end configured to engage the driven membrane 142. In order to permit the inlet actuator 168 to engage the driven membrane 142, a passage 172 is located in the lock ring 156 in alignment with the fluid inlet pathway 138.

The inlet actuator 168 is configured to move up and down, such as by a driving mechanism described in more detail below. In a first or up position, the nose of the inlet actuator 168 presses the driven membrane 142 against the bottom of the housing 126 of the disposable portion 122 of the pump 120 at the point where the fluid inlet pathway 138 intersects the bottom of the housing 126, thereby closing it. At this time, fluid is generally prevented from flowing between the fluid chamber 136 and the fluid inlet pathway 138.

When the inlet actuator 168 is in a second or down position, the driven membrane 142 preferably moves to a position in which it no longer blocks the fluid inlet pathway 138, as illustrated in FIG. 5. To provide sufficient space for downward movement of the driven membrane 142, the top surface of the lock ring 156 may be recessed at the location corresponding to the fluid inlet pathway, as illustrated.

When the fluid inlet pathway 138 is open, a fluid path is preferably defined between it and the fluid chamber 136. As illustrated, a fluid entry 174 may be defined for this purpose. The fluid entry 174 may comprise a path or channel defined in the bottom of the housing 126 which extends from the fluid chamber 136 to the space above the driven membrane 142 in the location of the fluid inlet pathway 138.

The outlet actuator 170 is generally similar to and operates similar to the inlet actuator 168. As illustrated, the outlet actuator 170 is configured to engage the driven membrane 142 in the location of the intersection of the fluid outlet pathway 140 and the bottom of the housing 126. The outlet actuator 170 extends through a passage 176 in the lock ring 156. A fluid exit 178, comprising a path or channel defined in the housing 126, preferably extends from the fluid chamber 136 to the space above the driven membrane 142 in the location of the fluid outlet pathway 140.

Preferably, the inlet and outlet actuators 170 are associated with the drive portion 124 of the pump. A drive mechanism is provided for effectuating movement of the inlet and outlet actuator 168,170.

FIG. 6 illustrates the pump 120 with the disposable portion 122 mounted to the drive portion 124 for operation. As illustrated, the bottom of the lock ring 156 rests upon the top of the drive portion 124. The flange 164 of the drive portion 124 extends into the opening 158 of the lock ring 156, so that the driving membrane 146 is positioned adjacent the driven membrane 142. When a vacuum is applied through the vacuum line 137, the driving membrane 146 and driven membrane 142 are vacuum coupled so that they move in unison.

Figure 7A:
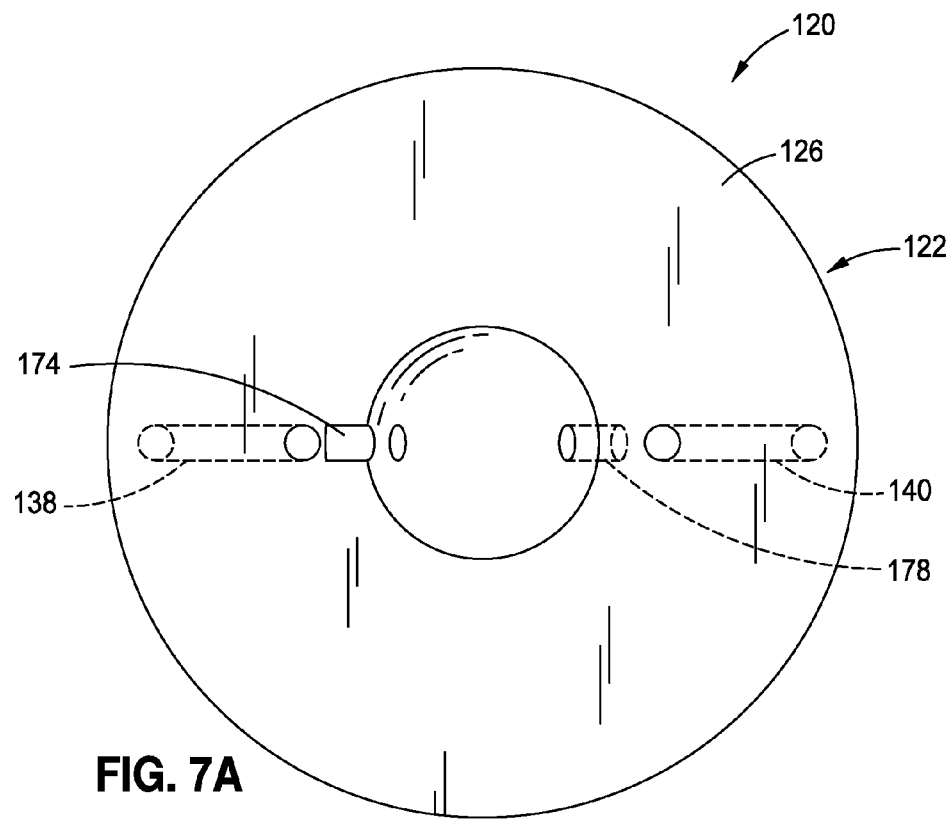
FIG. 7A is a bottom view of the disposable portion of the pump illustrated in FIGS. 5 and 6.
Figure 7B:
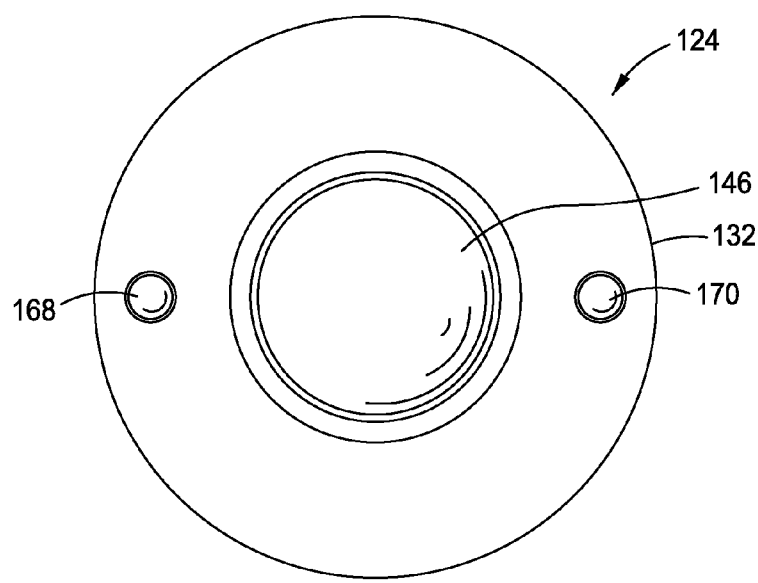
FIG. 7B is a top view of the drive portion of the pump illustrated in FIGS. 5 and 6.

FIGS. 7A and 7B additionally illustrate the disposable portion 122 and drive portion 124 of the pump 120. FIG. 7A is a bottom view of the disposable portion 122 or the pump 120. This figure illustrates the generally circular shape of the bottom of the housing 126 thereof, as well as the dome-shaped pump chamber 136. Further illustrated are the fluid inlet and outlet pathways 138,140. Also illustrated are the fluid entry 174 and fluid exit 178.

FIG. 7B is top view of the housing 132 of the drive portion 124 of the pump 120. This figure further illustrates the inlet actuator 168, outlet actuator 170, and driven membrane 146.

Additional aspects of the invention, including a method of pumping, will be described with reference primarily to FIG. 6. FIG. 6 is an assembled view of the pump 120 detailed above. In particular, as illustrated, the disposable portion 122 has been connected to or mated with the drive portion 124. At this time, the bottom of the lock ring 156 rests upon the top of the housing 134 of the drive portion 124. The upwardly extending flange 164 of the housing 134 extends into the opening 158 in the lock ring 156, whereby the driving membrane 146 is located adjacent to, or touches, the driven membrane 142.

In operation, a vacuum is applied to the vacuum line 137 to evacuate air from the space between the drive and driven membranes 146,142. In this manner, the two membranes are vacuum coupled and move with one another. A fluid source is connected to the pump 120, such as by connecting a fluid line leading from a fluid source to the fluid inlet 128 of the pump 120. Preferably, a similar fluid line is coupled to the fluid outlet 130 of the pump 120, whereby fluid may be delivered to a desired location, such as a patient.

Fluid is drawn into the pump chamber 136 from the fluid inlet 128 of the pump, through the fluid inlet pathway 138. In order to permit fluid to flow to the chamber, the inlet actuator 168 is moved to a downward or retracted position, thus allowing the driven membrane 142 to move away from the opening of the fluid inlet pathway 138. At that time, fluid may flow from the fluid inlet pathway 138 through the fluid entry 174 to the pump chamber 136. Inlet fluid flow is induced by downward movement of the driven membrane 142, as effectuated by downward movement of the driving membrane 146 by downward movement of the piston 144.

When fluid is being drawn into the fluid chamber 136, fluid is preferably prevented from flowing through the fluid exit 178. In particular, the outlet actuator 170 is moved to its raised position, forcing the driven membrane 142 over the opening to the fluid outlet pathway 140. This prevents fluid from being drawn backwardly through the pump from the fluid outlet 140 towards the fluid chamber 136.

Fluid is forced out of the pump chamber 136 by upward movement of the piston 144. As the piston 144 moves upwardly, it reduces the volume of the variable volume fluid chamber. This increases fluid pressure, forcing the driving membrane 146 upwardly, which in turn forcing the driven membrane 142 upwardly. This reduces the volume of the pump chamber 136. Fluid is permitted to flow through the fluid exit 178 by retraction of the outlet actuator 170. At that time, a fluid path is established from the fluid exit 178 to the fluid outlet pathway 140 to the fluid outlet 130 of the pump 120. In order to prevent fluid from being delivered backwardly to the fluid inlet 128, inlet actuator 168 is moved upwardly to close the fluid inlet pathway 138.

This process is then repeated. In particular, the piston 144 begins moving downwardly to again increase the volume of the pump chamber 136. The inlet actuator 168 is moved downwardly to permit the flow of fluid from the fluid inlet 128 to the pump chamber 136. The outlet actuator 170 is moved upwardly to prevent fluid from being drawn backwardly in the direction of the fluid outlet 130 to the pump chamber 136.

FIGS. 8A and 8B illustrate another embodiment of a disposable unit portion 222 a pump 20. As illustrated, the disposable portion 222 has a housing 226 having a top 223a and a bottom 223b. In use, the bottom 223b of the housing 226 would be placed against or mounted to a driving or pumping portion or unit, in similar fashion to that detailed above.

As illustrated, the disposable portion 222 again has a fluid inlet 228 and fluid outlet 230. In this embodiment, the disposable portion 222 defines a bubble trapping chamber 280 (the purpose of which is to catch air in the fluid and prevent it from reaching the pump chamber and being pumped through the pump) and a pump chamber 236. A fluid inlet pathway 238 extends from the fluid inlet 228 to the bubble trapping chamber 280, thereon to the pump chamber 236. A fluid outlet pathway 240 extends from the pump chamber 236 to the fluid outlet 230.

In the embodiment illustrated, the housing 226 is generally rectangular in peripheral shape. In one embodiment, various of the fluid pathways and/or chambers may be defined by raised or recessed areas. For example, when viewing the bottom of the disposable portion 222 as in FIG. 8A, the pump chamber 236 may appear as a depression in the housing 226. This depression, however, may be defined at least in part by a raised portion extending outwardly from the top of the housing 226, as illustrated in FIG. 8B.

FIG. 8C illustrates yet another embodiment of a disposable unit or portion 322 of a pump in accordance with the present invention. This embodiment disposable portion 322 is illustrated conceptually to illustrate various features which the disposable portion 322 may incorporate.

Once again, this embodiment disposable portion 322 includes a housing 326. The housing 326 defines a fluid inlet 328 and a fluid outlet 330. The disposable portion 322 further includes an air trap 380, a bubble detector 382 and a flow stop 384, as well as the pump chamber 336 (as defined by the housing 326 and a driven membrane 342 in cooperation with the housing 326).

As indicated above, the air trap 380 is preferably configured to trap air in the fluid which is drawn into the pump. Air which is trapped in the air trap 380 may be expelled manually or automatically, such as through a port or valve to the exterior of the housing 326 of the disposable portion 322.

The bubble detector 382 is preferably configured to detect bubbles in the fluid. The detector 382 is preferably located along an upward fluid outlet path, to avoid "floating" bubble false alarms. The bubble detector 382 may comprise a chamber having a reflective side wall and transmitter/receiver.

In one embodiment, the disposable portion 322 may also comprise a fluid pressure sensor. The sensor may be configured to detect fluid inlet and/or outlet pressure.

As indicated above, in various embodiments, one or more drive mechanisms or devices may be provided for moving the various elements of the pump. For example, referring to the embodiment pump 120 illustrated in FIGS. 5 and 6, the inlet and outlet actuators 168,170 and the piston 144 may be selectively moved in order to effectuate operation of the pump 120. Various embodiments of drive mechanisms will now be described with reference to FIGS. 9A-9D.

Figure 9A:
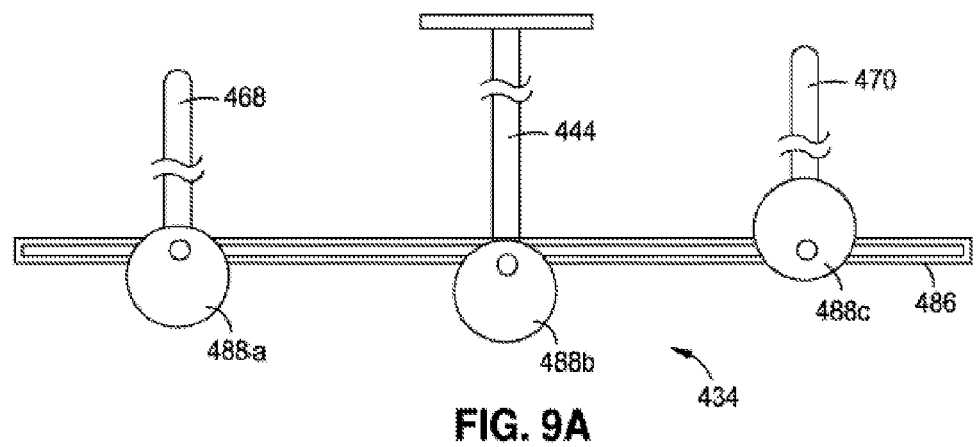
FIG. 9A illustrates a first drive mechanism in accordance with an embodiment of the present invention.

FIG. 9A illustrates a cam-type drive mechanism 434. As illustrated, a drive member 486 is configured to move cam elements corresponding to each of the members to be driven. In the embodiment illustrated, corresponding to a pump configuration such as that illustrated in FIGS. 5 and 6, where there is an inlet actuator 468, an outlet actuator 470, and a piston 444. As illustrated, a first cam member 488a is associated with the inlet actuator 468, a second cam member 488b is associated with the piston 444 (though it could be configured to directly engage the bellows), and a third cam member 488c is associated with the outlet actuator 470. The cam members 488a, 488b, 488c are configured to be moved by the drive member 486 in a desired path. As illustrated, each cam member has a pin which engages a track in the drive member 486. The pin corresponding to each cam member may be offset from a central axis, whereby the path of the periphery of the cam member is non-circular. Each of the inlet actuator 468, outlet actuator 470 and piston 444 are configured to follow those respective paths, whereby they may be moved up and down. Of course, the movement is timed so that, for example, the pump 220 illustrated in FIGS. 5 and 6 operates as described.

Though not shown, one or more drives may be provided for moving the drive member 486. Such drives may have a variety of configurations and be powered in a variety of manners, such as mechanically or electrically.

The drive mechanism is preferably associated with the drive portion of the pump of the invention. In one embodiment, the drive mechanism may be connected to the drive portion, such as an in a manner permitting the drive mechanism and drive portions to be separated. In another embodiment, the drive mechanism is preferably integral with the drive portion, such as being located in a lower portion of the housing thereof.

Figure 9B:
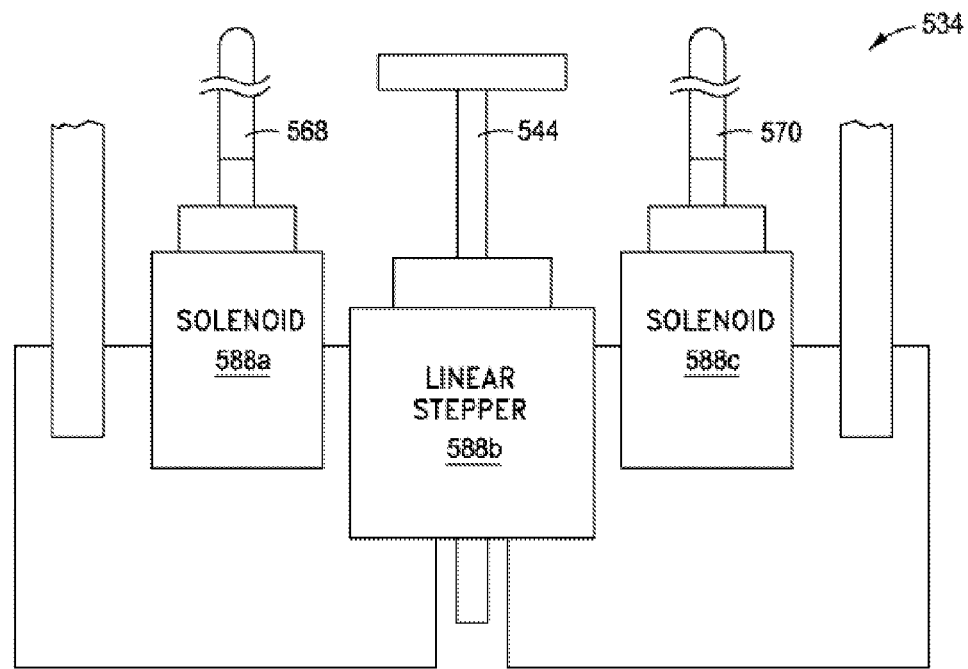
FIG. 9B illustrates a second drive mechanism in accordance with another embodiment of the invention.

FIG. 9B illustrates a solenoid drive mechanism 534. As illustrated, a first drive 588a in the form of an electrically powered solenoid is provided. The first drive 588a preferably moves a drive rod, which in turn drives or moves the inlet actuator 568. Likewise, a third drive 588c is in the form of an electrically powered solenoid. The third drive 588c preferably also includes a drive rod. That drive rod moves the outlet actuator 570. Lastly, in one embodiment, a second drive 588b has the form of a stepper motor, and is configured to move or drive the piston 544.

In general, the solenoids comprising the first and third drives 588a,c may be configured to move their associated drives between extended and refracted positions. Preferably, those positions correspond to the extended and retracted positions of the inlet actuator 568 and outlet actuator 570.

In a preferred embodiment, the second drive 588*b* has the form of a linear stepper motor in order to allow the piston 544 to be moved to various positions (such as a retracted and a plurality of extended positions between the retracted and a maximum extended position). In this manner, the position of the piston 444 may be selectively controlled (such as for controlling the pumping volume and cycle time, as detailed below).

Figure 9C:
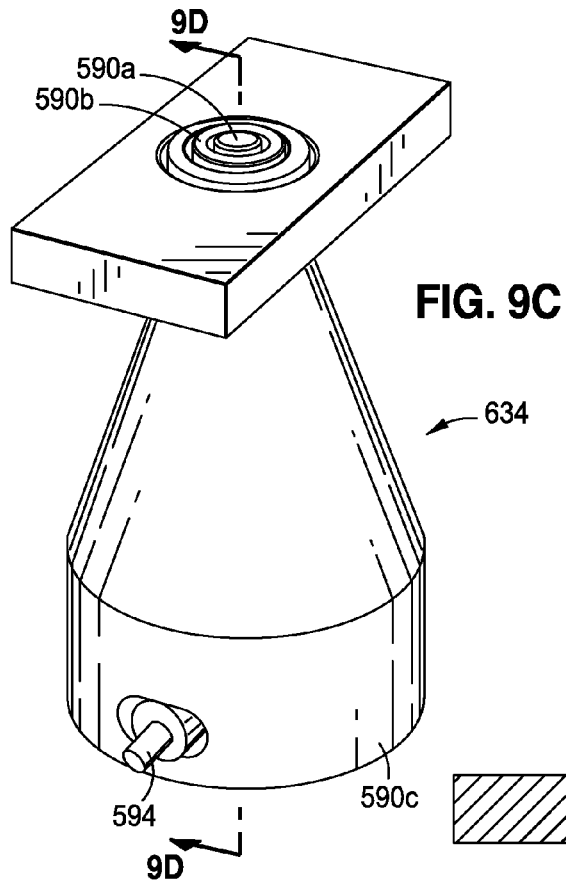
FIGS. 9C and 9D illustrate a third drive mechanism in accordance with yet another embodiment of the invention.
Figure 9D:
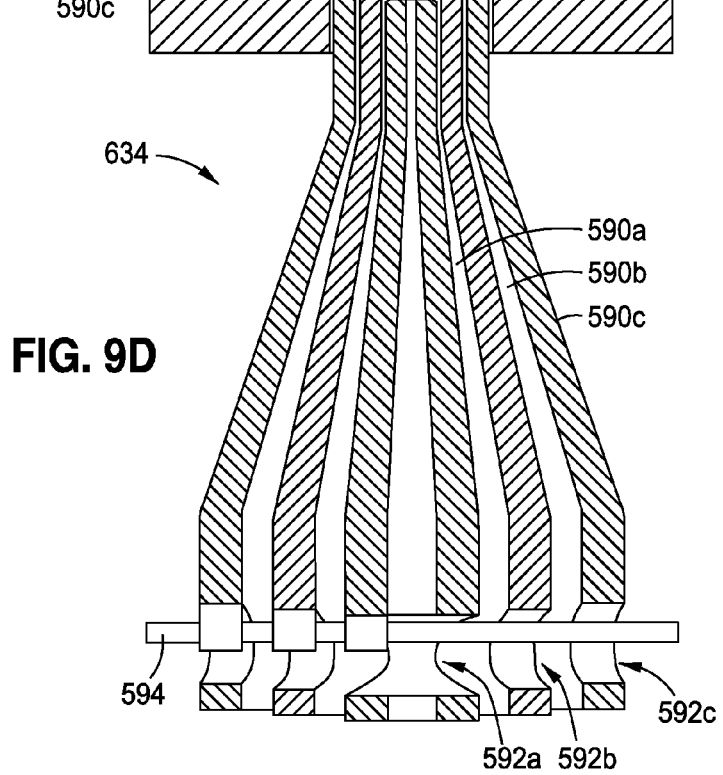

FIGS. 9C and 9D illustrate yet another embodiment of a drive mechanism. In this embodiment, the drive mechanism 634 is configured to directly drive the drive or driving membrane, rather than drive that membrane indirectly, such as via fluid associated with a variable volume chamber.

As illustrated, this drive mechanism 634 comprises multiple actuators. Preferably, the actuators are nested. In particular, in one embodiment, the drive mechanism 634 comprises a first actuator 590*a*, a second actuator 590*b*, and a third actuator 590*c*. The first actuator 590*a* is located or housed at least partially within the second actuator 590*b*, which in turn is located or housed at least partially within the third actuator 590*c*.

In one embodiment, the first, second and third actuators 590*a*, 590*b*, 590*c* are generally conical in shape, having a first or top end and a second or bottom end, the first end being smaller in dimension than the second end. Preferably, the actuators are sized to permit their relative and at least partial independent movement, i.e. to permit the first actuator 590*a* to move within the second actuator 590*b*, to permit the second actuator 590*b* to move with respect to the first and third actuators 590*a*, 590*c*, and to permit the third actuator 590*c* to move relative to the second actuator 590*b*.

In a preferred embodiment, the actuators can be moved between at least extended and retracted positions, and preferably one or more positions there between. When used with a pump such as that illustrated in FIGS. 5 and 6, the extended and retracted positions may correspond to raised or upper, and refracted or lower, positions.

The drive mechanism includes a driving device configured to move the actuators. In one embodiment, each of the actuators defines a passage 592*a*, 592*b*, 592*c* through the second or bottom end thereof. A cam-type drive shaft 594 extends there through. Rotation or other movement of the shaft 594 preferably effectuates movement of the actuators 590*a*, 590*b*, 590*c*. In one embodiment, the shaft 594 defines a plurality of cams thereon, at least one cam corresponding to each of the actuators and configured to move the corresponding actuator in a specific pattern. Of course, other means might be provided for moving the actuators, such as solenoids, linear stepper motors or other mechanical or electromechanical drives.

Of course, the drive might have fewer than three or more than three actuators. Further, the shape of those actuators might vary. Preferably, however, each actuator is configured to engage and move a portion of the drive membrane.

A particular advantage of this embodiment drive mechanism is that movement of the drive membrane is effected without the need for a variable volume chamber or fluid. Instead, movement of the membrane is effected directly.

In addition, an advantage of multiple actuators is that the amount of force applied to the drive membrane may be closely controlled by controlling how many of the actuators are moved and the extent of their movement. In this manner, movement of the driven membrane may be closely controlled, thus allowing the fluid flow characteristics to be carefully controlled. In addition, the actuators 590*a*, 590*b*, 590*c* may selectively be moved in the forward or reverse (up or down) directions, again allowing significant control over pumping.

The pump and method of pumping or moving fluid may have numerous other embodiments in accordance with the invention.

In one embodiment, the pump of the invention has two main portions: a fluid contacting portion, which is referred to herein as a disposable unit or portion, and a drive portion. However, the pump may have more than two portions. For example, the pump may have three portions, such as a disposable fluid-contacting portion, an actuating portion (such as including the inlet actuator, outlet actuator and piston), and a drive portion (such as containing solenoids and stepper motors or a cam drive or the like).

Preferably, the drive portion of the pump is computer controlled, whereby the displaced volume of the pump chamber may be controlled. For example, a computer may be utilized to control the multiple actuators 590*a*, 590*b*, 590*c* of the embodiment pump illustrated in FIG. 9D or the stepper motor 588*b* illustrated in FIG. 9B, whereby the change in volume of the pump chamber of the pump may be varied over time in a controlled manner.

The pump may be constructed from a variety of materials and in a variety of manners. In a preferred embodiment, the disposable portion is constructed to be disposable, i.e. preferably to have a low cost. For example, the disposable may be constructed of a thermo-plastic material and, as detailed herein, have a simple configuration (such as the sole moving part comprising the driven membrane).

As indicated herein, the pump may be configured to include a number of features, such as an air trap, a bubble sensor, a flow rate sensor, one or more pressure sensors, a flow stop, or combinations thereof. The configurations of these features may vary. For example, various types of pressure sensors may be utilized as part of the pump. Such sensors may be utilized, for example, to measure intake, outlet and, in the case of fluid actuator, the fluid pressure. In the latter case, the intake and output pressures may be inferred from the fluid actuator pressure, eliminating the need for secondary sensors. In one embodiment, the pump may include a vacuum pressure sensor. Such a sensor may be utilized to detect or determine the pressure within the vacuum line(s). The sensor could be associated with or comprise a switch, such as coupled to the vacuum source, for causing the source to be activated when the pump is turned on and/or to be activated in the event vacuum pressure falls below a minimum level.

As indicated above, various drive devices or mechanisms may be utilized to actuate the pump. Various embodiments have been described and illustrated herein, but others are possible.

The portions of the pump, such as the housings of the disposable portion and drive portion, may have a variety of shapes and sizes. The shapes and sizes of the portions may vary depending on various design criteria.

In a preferred embodiment, the pump includes fluid flow controls to control the flow of fluid there through. As indicated, the fluid flow controls may comprise one or more actuated valves. Other types of fluid flow controls than specifically illustrated herein might be utilized. For example, the actuators might be configured to extend directly into and out of inlet and outlet fluid paths to selectively obscure them.

In a preferred embodiment, the disposable portion of the pump has a single driven membrane. This single membrane is used as a pump member and as a valving member for the intake and outlet fluid paths. The disposable portion might utilize more than one membrane, however, such as a first membrane at the pump chamber, a second in conjunction with the fluid inlet path for serving as the inlet control valve, and a third in conjunction with the fluid outlet path for serving as the outlet control valve.

In one embodiment, the driven membrane may be separated from the disposable portion. In this embodiment, after the disposable portion is used, the driven membrane might be thrown away and the remainder of the disposable portion might be sterilized for reuse. After sterilization, a new driven membrane would be associated with the disposable portion.

In one embodiment, the driving membrane is moved by fluid. As described above and illustrated herein, movement of a piston may change the volume of a chamber containing fluid, which chamber is bounded in at least one area by the driving membrane. In one embodiment, such as illustrated in FIG. 1, the piston itself may bound a portion of the chamber, whereby movement of the piston directly changes the volume of the chamber. In another embodiment, as illustrated in FIG. 4, the piston may move a boundary of the chamber. In that embodiment, the piston moves a portion of the chamber bounded by a bellows. Of course, the driving membrane might be moved in other manners. For example, fluid might be pumped into the chamber or be released from the chamber to change the fluid volume therein. The driving membrane may also be moved directly.

In the preferred embodiment, the driving and driven membranes comprise relatively thin, flexible members. The material from which the membranes are constructed may vary. Further, the membranes may have forms other than generally constant thickness material bodies, but may comprise other members which are sufficient resilient to move up and down in response to applied forces.

In one embodiment, the disposable portion might be configured with integral external fluid lines or fluid connectors for mating with external devices (such as a fluid source or line).

In one embodiment, the driving membrane is indirectly driven, such as by fluid located in a variable volume chamber. In other embodiments, however, the driving membrane may be directly driven.

In one embodiment, the air trap is configured with a sensor to detect or determine when a predetermined amount (such as a maximum amount) of air is contained therein. When such a level or amount of air is sensed, the air may be expelled from the air trap, such as back to a fluid source drip chamber. This may be accomplished by operation of a solenoid or linear actuator, preferably while the inlet valve is closed to avoid any interruption of fluid flow to the patient.

Various aspects of the invention will now be appreciated. First, one aspect of the invention is a fluid pump having at least two portions, a portion which is configured to contact the fluid to be pumped, and another portion. Preferably, the pump has a first portion comprising the pumping or drive portion, and a second fluid contacting portion which can be selectively connected to or disconnected from the drive portion. Advantageously, this allows the fluid-contacting portion to be disposed of after use, or sterilized after use, while the remaining portion of the pump, such as the pumping portion, can be re-used with a new fluid-contacting portion or a sterilized fluid-contacting portion of the pump.

In one embodiment, the fluid-contacting portion of the pump is configured to be "disposable." In particular, the design of that portion of the pump is configured to be simple, whereby it may be relatively inexpensive to manufacture. This allows that portion to be cheaply replaced (avoiding the costs and steps associated with having to sterilize for reuse).

In one embodiment, the disposable may be constructed at least partly of a plastic material for this purpose, such as in a molding process.

Another aspect of the invention is a multi-piece pump where pumping is facilitated through the use of one or more engaging membranes or diaphragms or other flexible members. Preferably, these members are configured to move in unison via a vacuum coupling. The vacuum coupling has the advantage that it is a simple and inexpensive coupling configuration. For example, such a configuration avoids the need for complex mechanical connections of elements as is common in pump drives. In addition, the vacuum coupling provides a simple way of disconnecting the pump portions, in that there is no need to disconnect particular linkages or elements.

Advantageously, the pump of the invention can be configured to be highly compliant. Further, fluid flow rates or volumes, and pressure, may be very closely controlled using the pump of the invention.

A significant benefit of the pump of the invention is the highly elastic membrane of the disposable portion of the pump. This feature minimizes the dimensional accuracy required of the disposable portion, thus reducing significantly the complexity and cost of manufacture, and thus ultimate cost of the disposable portion.

A significant benefit of the vacuum coupling is that the coupling enables the pump to pump against negative output pressures and to aspire fluid from containers lower than the pump (functions which would not otherwise be possible—i.e. the advantages of the disposable portion detailed above are realized or enabled by the vacuum coupling).

Another feature and advantage of the invention is a pre-pump chamber which assists in trapping and eliminating air bubbles which may form in the fluid itself or travel into to the pump from the fluid source.

It will be understood that the above described arrangements of apparatus and the method there from are merely illustrative of applications of the principles of this invention and many other embodiments and modifications may be made without departing from the spirit and scope of the invention as defined in the claims.

What is claimed is:

1. A fluid pump comprising:
   a drive unit comprising a housing and a plurality of actuators each configured to move between at least a respective first and a respective second position, wherein the plurality of actuators are coaxially nested and are generally conical in shape with first ends and second ends that are larger in dimension than the first ends, wherein a first actuator of the plurality of actuators is at least partially within a second actuator of the plurality of actuators and the first end of the first actuator is smaller in dimension that the first end of the second actuator; and
   a driven unit comprising a housing, a fluid path leading from a fluid inlet to a fluid outlet, and at least one driven membrane defining a portion of the fluid path, the driven unit configured to be selectively coupled to the drive unit so that a portion of the driven membrane is coupled to each of the plurality of actuators, whereby movement of at least one of the plurality of actuators effectuates movement of the driven membrane, causing fluid to be pumped through the driven unit from the fluid inlet to the fluid outlet, wherein the first ends of the plurality of actuators are proximate to the driven unit.

2. The fluid pump of claim 1, wherein the first ends of the plurality of actuators are substantially circular in shape.

3. The fluid pump of claim 1, wherein the plurality of actuators are configured to permit at least partially independent movement of each of the plurality of actuators.

4. The fluid pump of claim 1, wherein:
the plurality of actuators each comprise a passage;
the drive unit further comprises a drive shaft comprising a plurality of cams coupled to a shaft;
the drive shaft is disposed through the passages of the plurality of actuators such that at least one of the plurality of cams corresponds to each of the plurality of actuators and is configured to move the corresponding one of the plurality of actuators in a specific pattern; and
rotation of the drive shaft effectuates movement of the plurality of actuators.

5. The fluid pump of claim 1, further comprising a plurality of solenoids wherein each of the plurality of solenoids is configured to move at least one of the plurality of actuators.

6. The fluid pump of claim 1, further comprising a plurality of linear stepper motors wherein each of the plurality of stepper motors is configured to move at least one of the plurality of actuators.

7. The fluid pump of claim 1, further comprising a plurality of electro-mechanical drives wherein each of the plurality of drives is configured to move at least one of the plurality of actuators.

8. A method of pumping fluid, the method comprising the steps of:
coupling a driven unit between a fluid source and a destination, the driven unit comprising a housing, a fluid path leading from a fluid inlet coupled to the fluid source to a fluid outlet coupled to the destination, and at least one driven membrane defining a portion of the fluid path;
coupling a drive unit to the driven unit, the drive unit comprising a housing and a plurality of actuators each configured to move between at least a respective first and a respective second position, wherein the plurality of actuators are coaxially nested and generally conical in shape with first ends proximate to the driven unit and second ends that are larger in dimension than the respective first ends, wherein a first actuator of the plurality of actuators is at least partially within a second actuator of the plurality of actuators and the first end of the first actuator is smaller in dimension that the first end of the second actuator, the drive unit and driven unit configured such that a portion of the driven membrane is coupled to each of the plurality of actuators; and
moving at least one of the plurality of actuators between the respective first position and the respective second position, thereby moving the driven membrane, thereby causing fluid to be pumped through the driven unit from the fluid source to the destination.

9. The method of claim 8, wherein the first ends of the plurality of actuators are generally circular in shape.

10. The method of claim 8, wherein the plurality of actuators are configured to permit at least partially independent movement of each of the plurality of actuators.

11. The method of claim 8, wherein the step of moving at least one of the plurality of actuators comprises rotating a drive shaft comprising a plurality of cams coupled to a shaft, wherein the drive shaft is disposed through a passage of each of the plurality of actuators such that at least one of the plurality of cams corresponds to each of the plurality of actuators and is configured to move the corresponding one of the plurality of actuators in a defined pattern.

12. The method of claim 8, wherein the step of moving at least one of the plurality of actuators comprises moving at least one of a plurality of solenoids wherein each of the plurality of solenoids is coupled to at least one of the plurality of actuators.

13. The method of claim 8, further comprising moving at least one of a plurality of linear stepper motors wherein each of the plurality of stepper motors is coupled to at least one of the plurality of actuators.

14. The method of claim 8, further comprising moving at least one of a plurality of electro-mechanical drives wherein each of the plurality of drives is coupled to at least one of the plurality of actuators.

\* \* \* \* \*